United States Patent
Guehring et al.

(10) Patent No.: US 9,208,747 B2
(45) Date of Patent: Dec. 8, 2015

(54) CONTROL MODULE AND CONTROL METHOD TO DETERMINE PERSPECTIVE IN THE RENDERING OF MEDICAL IMAGE DATA SETS

(71) Applicants: Jens Guehring, Erlangen (DE); Stephan Nufer, Erlangen (DE)

(72) Inventors: Jens Guehring, Erlangen (DE); Stephan Nufer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 235 days.

(21) Appl. No.: 13/959,960

(22) Filed: Aug. 6, 2013

(65) Prior Publication Data
US 2014/0035811 A1 Feb. 6, 2014

(30) Foreign Application Priority Data
Aug. 6, 2012 (DE) .......................... 10 2012 213 910

(51) Int. Cl.
| G09G 5/00 | (2006.01) |
| G06F 3/147 | (2006.01) |
| G06F 3/0482 | (2013.01) |
| G06F 19/00 | (2011.01) |

(52) U.S. Cl.
CPC .............. *G09G 5/006* (2013.01); *G06F 3/0482* (2013.01); *G06F 3/147* (2013.01); *G06F 19/321* (2013.01); *G09G 2340/12* (2013.01); *G09G 2354/00* (2013.01); *G09G 2380/08* (2013.01)

(58) Field of Classification Search
CPC ...................... A61B 2019/5289; A61B 6/5247; A61B 6/5235; A61B 6/463; A61B 6/5223; A61B 8/5238; G06T 2210/41; G06T 2200/24; G06F 19/321; G06F 19/3406; G06F 19/3437
See application file for complete search history.

(56) References Cited

U.S. PATENT DOCUMENTS

| 2003/0026503 A1* | 2/2003 | Kallergi et al. ............... 382/299 |
| 2003/0071829 A1* | 4/2003 | Bodicker et al. .............. 345/619 |
| 2006/0132508 A1* | 6/2006 | Sadikali ........................ 345/665 |
| 2006/0242143 A1* | 10/2006 | Esham et al. ..................... 707/6 |
| 2012/0131498 A1 | 5/2012 | Gross et al. |

* cited by examiner

*Primary Examiner* — Dorothy Harris
(74) *Attorney, Agent, or Firm* — Schiff Hardin LLP

(57) ABSTRACT

In a control method and a control unit for context-specific determination of at least one DESIRED perspective upon rendering of medical image data at a monitor, a graphical symbol is generated at a user interface dynamically and depending on an image status in order to detect a perspective control signal, and is used to control the rendering.

8 Claims, 2 Drawing Sheets

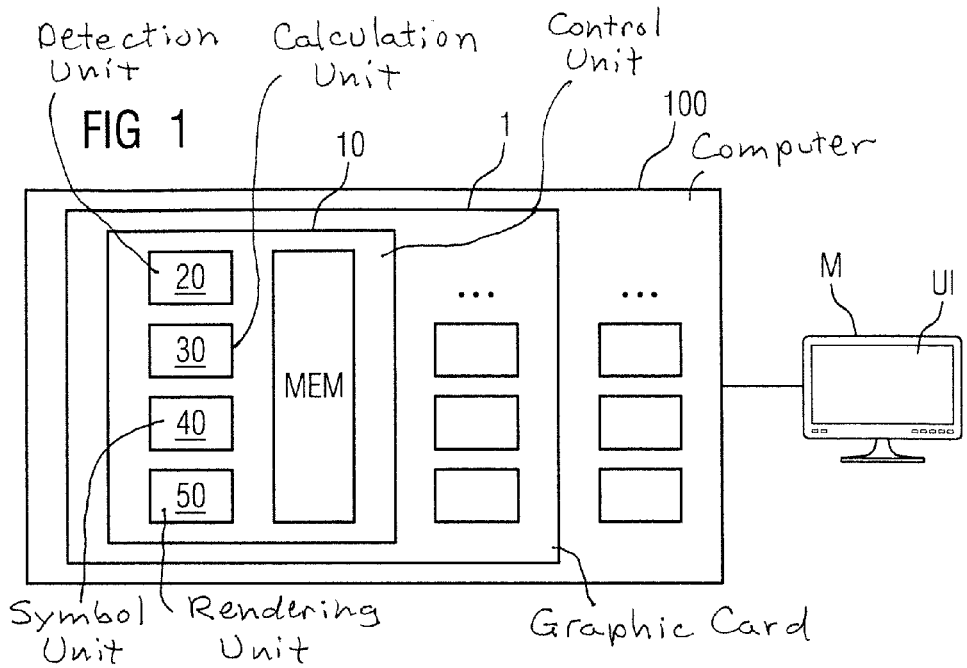
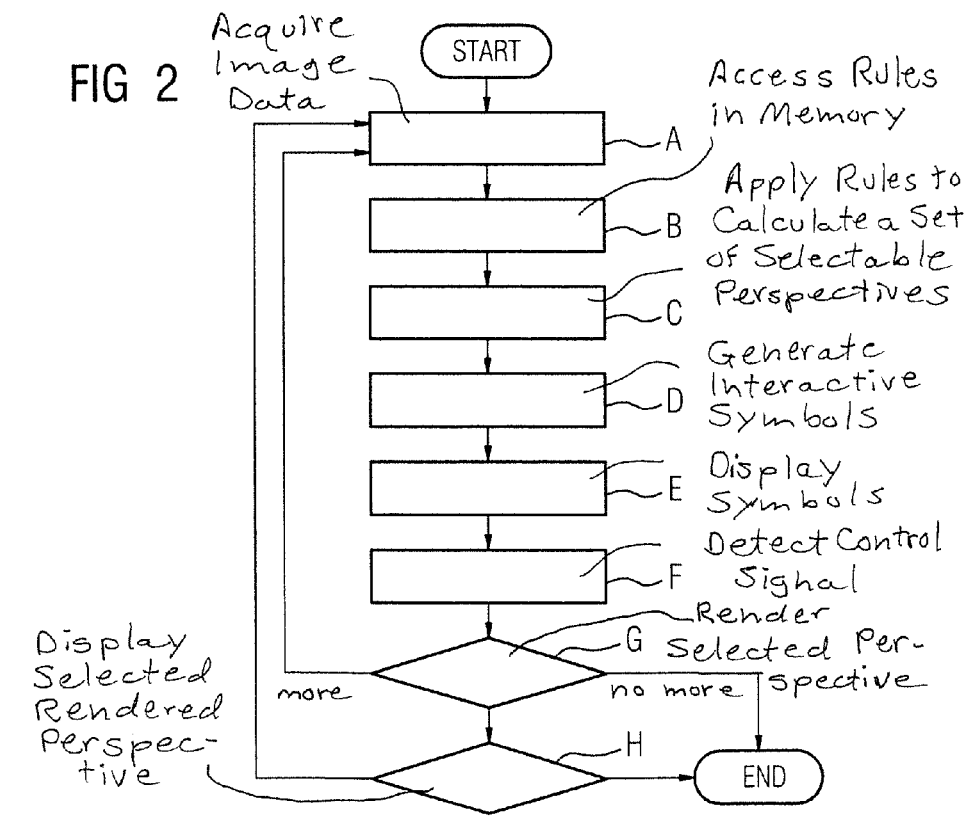

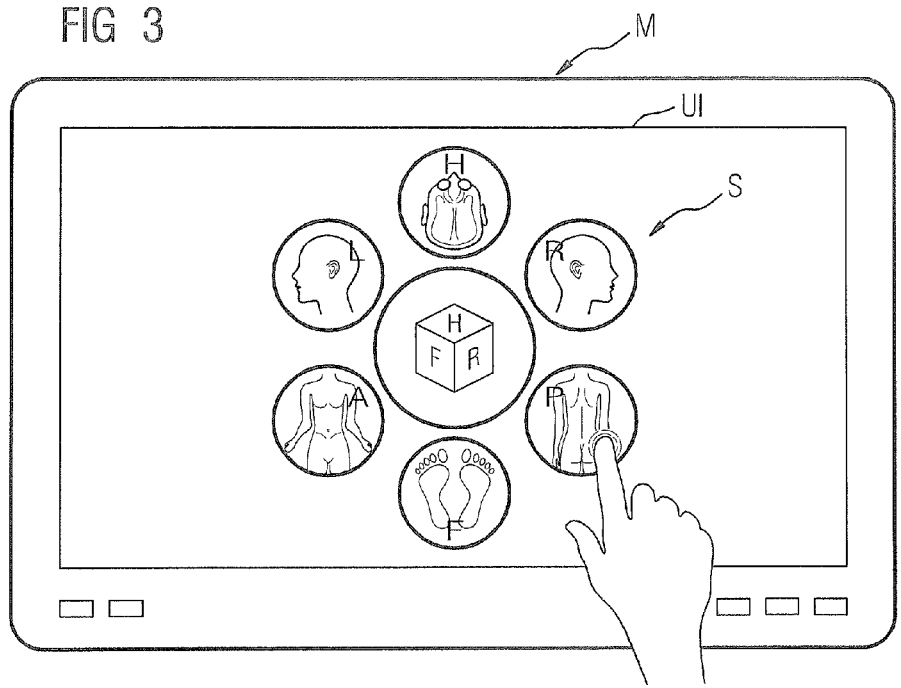
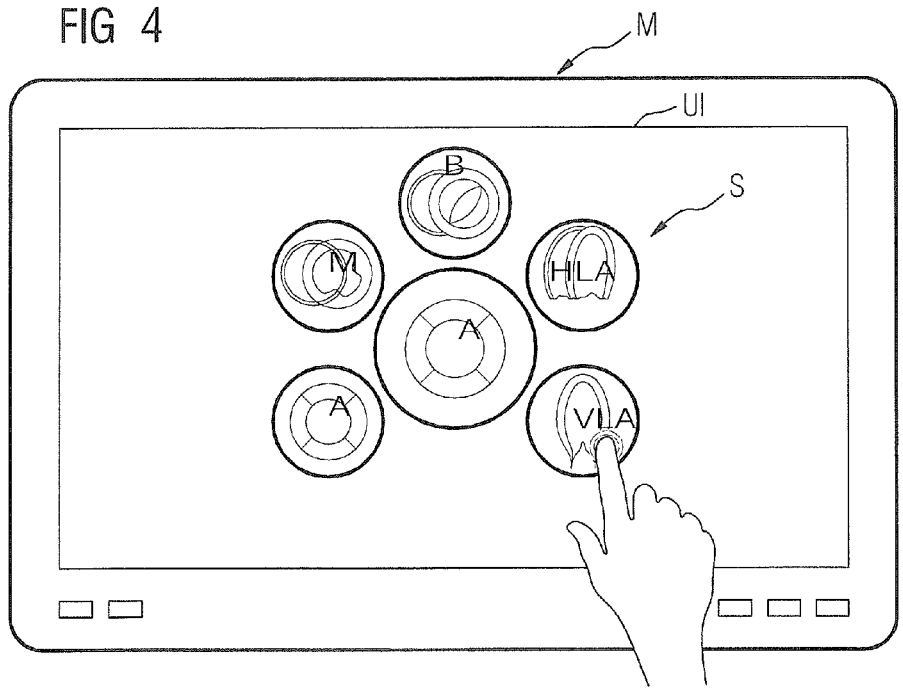

CONTROL MODULE AND CONTROL METHOD TO DETERMINE PERSPECTIVE IN THE RENDERING OF MEDICAL IMAGE DATA SETS

BACKGROUND OF THE INVENTION

1. Field of the Invention

The present invention is in the fields of image processing and medical engineering and in particular concerns an approach to determine in advance the perspective(s) that should be the basis of a downstream rendering process in order to present medical image data sets in a specific perspective on a monitor.

2. Description of the Prior Art

Particularly in the field of medical engineering, it is an indispensable requirement, for example within the scope of assessing image data, that the image data sets are also presented in the relevant perspective on a monitor. The selection of the anatomical orientation and the presentation format are important factors. Medical image data are acquired by different types of acquisition apparatuses (known as modalities), for example computed tomography systems, magnetic resonance tomography systems, positron emission tomography systems, etc. Raw image data are acquired by the imaging apparatuses, and the raw image data are then transformed via different image processing processes into two-dimensional or multi-dimensional images.

For example, multi-planar reconstruction methods (MPR methods) can be used for this purpose in order to also show the presented data from other perspectives or orientations on the monitor. Depending on which medical process is to be implemented (for example a differential diagnosis or a direct assessment of the acquired image data, etc.), it is necessary to determine the respective perspective or view in which the acquired image data should be presented at the monitor.

Known methods to determine the respective orientation or perspective in which the image data should be presented are typically based on the representation of a cube or another user interface element that which the user can select from a list of text entries after a mouse click. These methods have the disadvantage that they are not optimal for user interfaces that are controlled by direct manipulation, thus interactive user interfaces or touch-sensitive surfaces (touchscreens, for example). This is because a selection of written, list-structured menus and sub-menus is most often difficult to operate for a touchscreen (since it is not precise enough). Furthermore, it is a problem that the entries to be selected are based on a text description of the perspective.

For example, if a viewer would like to see a three-dimensional MRT data set of a human head in a transverse view, selection menus for the determination of the perspective are offered to the viewer according to the aforementioned selection method according to the prior art. For example, here the viewer can select specific entries from a list structure in order to determine from which perspective the viewer would like to view the three-dimensional image series. Since 5, 6 or more perspectives are typically available, the selection can be difficult, particularly in the case of a small screen.

A further difficulty is that the list-based selection shows a written naming of technical medical terms (for example anterior-posterior, head-feet, or in the case of heart examinations, four-chamber view, two-chamber view, etc.). Since these terms are specific to a country's language, and specific image data, examination types and/or forms of assessment require a specific selection of perspectives, different display configurations are necessary depending on the modality, examination type and/or assessment, which makes the computer product expensive overall (this is in part because the technical terms must be translated into a respective language, and mix-ups can easily occur in the selection of similar menu entries, and since specific perspectives are reasonable only for certain specific examinations and make no sense for other examinations. For example, it is thus not reasonable to offer perspectives that are relevant to the heart (for example two or four chamber views) in the case of an orthopedic knee examination).

A significant disadvantage of such known methods is also that the context of the respective examination and/or finding with the respective acquired image data has not been taken into account in the perspective control.

SUMMARY OF THE INVENTION

An object of the invention is to improve the control of the rendering process of medical images with regard to the perspectives to be selected. In particular, a perspective selection should be possible that is also usable by touch user interfaces. Furthermore, the likelihood of the viewer making an incorrect perspective selection, due to a sub-optimal presentation of the selection options, should be reduced.

In the following, the achievement to the object is described with regard to the inventive method. Features, advantages and/or alternative embodiments that are mentioned are also applicable to the other aspects of the invention, and vice versa. In other words: the control unit and the storage medium can also be developed with the features that are described in connection with the method. The functional features of the method correspond to substantive computer-implemented modules, in particular microprocessor modules of units of a device. For example, these can be implemented in a graphic card of the computer system. The control unit can be integrated as an embedded system into a graphic card and/or into a computer-implemented finding system.

According to one aspect of the invention, the object achievement refers to a computer-based control method to select perspectives in the rendering of medical image data sets in a DESIRED perspective for presentation on a monitor. The method includes the following steps:

Acquire the respective image data set and an image status associated with the image data set. Alternatively, it is also possible that an image data set is already shown on the monitor (in a REAL perspective), which image data set is to be changed or retained by the control method. In this case, the presented image data set and the associated image status are detected.

Access a memory in which rules are stored in order to determine a set of selectable perspectives depending on the detected image status. In the event that the image is already shown on the monitor (see above), the REAL perspective of the already rendered image is additionally determined.

Calculate the set of selectable perspectives based on the access to the memory. This thereby involves a selection of perspectives that are relevant to the respective context of the image data (display).

Dynamic generation of an interactive symbol for graphical representation of the calculated set of selectable perspectives. The interactive symbol is advantageously a graphical representation of perspectives that are directly and intuitively understandable even without comprehension of a text. The generated symbol is interactive. It can include buttons (control areas) since it is designed to detect input signals of the user. In particular, a specific region of the symbol that represents a specific perspective can be activated by making a mouse click.

Overlay the interactively generated symbol in a user interface for the selection of a DESIRED perspective from the calculated set of selectable perspectives that are represented with the symbol.

Detect a perspective control signal at the overlaid, interactive symbol to determine the DESIRED perspective.

Render the image data set in the determined DESIRED perspective, based on the detected perspective control signal.

The invention thus concerns the generation of a user interface element to control a rendering process in which a perspective is to be determined, from which the image data should be rendered. Furthermore, the invention concerns the control of the rendering on the basis of interactions via the generated user interface element. The user interface element is a symbol, and not a written selection menu (and possibly with sub-menus) structured like a list. The symbol is dynamically generated for each process, specific to the application and image data. The symbol can include icons and/or letters. The letters can be single letters or letter combinations that, however, do not inherently form a text entry (for example not a separate word or word combination). The symbol can include at least one sensor element. The sensor element can be a touch-sensitive user interface sensor. In the preferred embodiment of the invention, the symbol includes buttons that can be activated as I/O buttons for interaction. The size and/or shape of the symbol and/or the buttons can be configured. The control method or, respectively, the control unit according to the invention interacts (or, respectively, exchanges digital data) with a symbol processor in which are stored rules, data and a processor for processing symbol-related and/or perspective-related data.

In the following, the terms used herein are explained in detail.

The method serves to determine perspectives in the rendering of images. An orientation in which the images are presented on the monitor is therefore determined. According to the invention, a differentiation is made between a REAL perspective and a DESIRED perspective. The term "REAL perspective" refers to the perspective of the currently presented image or, respectively, image data set. In this case (thus in the event that an image is already shown in a perspective on the monitor), the method is applied as a perspective change method in order to determine future perspectives in the presentation. In the event that such an image is not yet shown on the monitor, the method is used as an initial control method to determine the (first) perspective. The DESIRED perspective is selected by the user and serves for the calculation of the image data set. Naturally, it may occur that the REAL perspective coincides with the DESIRED perspective; although the user/viewer is then offered a perspective change via the overlay of the symbol, he does not use this to retain the original perspective.

For example, different reconstruction methods (in particular multiplanar reconstruction) can be applied in the calculation of the image data set. Alternatively, projection methods can also be used—for example maximum intensity projection (MIP) or minimum intensity projection (mIP)—in order to generate reconstructed slice exposures (for example from an MRT acquisition). Modern reconstruction methods are not limited to the three spatial axes in the selection of the perspective; rather, non-orthogonal planes can also be determined as a perspective in order to be able to depict specific anatomical structures that would otherwise be covered by other tissue structures. Within the scope of the finding, it is very significant to determine the correct perspective in order to be able to also display all medically relevant data.

According to a preferred embodiment of the invention, the presentation medical image data sets have been acquired by different modalities (CT, MRT, ultrasound, PET etc.). These can be two-dimensional, three-dimensional or higher-dimensional image data sets. The image data to be presented can also originate from a heart examination (for example a cardiac catheter examination) or have been acquired with functional methods (for example fMRT or SPECT, etc.).

The "image status" designates a vector with different parameters. Information about the respective modality of the image data (CT, MRT, ultrasound etc.), the type or purpose of the image viewing (such as an assessment with regard to content, or a purely formal, cursory review of the image data set for errors or review to the effect of whether these exist at all and/or have been stored). The image status moreover advantageously includes information about the respective examined organ (for example heart, knee, liver, entire abdomen etc.). Furthermore, the image status can also designate a position of the image data in the human body. It can be an anatomical specification. For example, this position then indicates that the image data sets originate from an anatomical structure that is located in the head of the patient or in the leg of the patient, for example. Additional data that are relevant to the selection of the respective perspective can then be derived (advantageously automatically) from these specifications. In a preferred embodiment, metadata of the respective image data sets are also analyzed, in particular when the data are present in the DICOM (DICOM: Digital Information and Communications in Medicine) format.

In a preferred embodiment, the detection of the image status thus includes additional automatically executed method steps. Individual parameters of the image status are derived from other data, for example from the metadata. For this purpose, a rule base can be accessed and used, that is stored in a specific memory (local or remote), for example.

The image status includes information with regard to the modality with which the image data have been acquired; with regard to the type of examination; with regard to the examined organ; with regard to the type of assessment; with regard to the position; and/or with regard to the context of the image data. According to the invention, it is thus detected whether the image data are (for example) image data of a cardiac examination or reconstructed MRT image data of a knee examination. This image status has a significant influence on the selectable perspectives in the subsequent presentation.

According to a preferred embodiment, a configuration phase is provided that is upstream of the perspective determination or execution phase, and in which it can be configured which parameters are to be considered for the image status. Defined parameters are pre-configured that are used for the calculation of the image status. These parameters include at least: the position of the examined organ or, respectively, the anatomical structure, the type of acquiring modality or, respectively, the type of acquired image data, the type of finding.

The image status is automatically calculated without user inputs being required.

Among other things, a set of selectable perspectives is calculated from this image status. For example, it is incorporated into this that—given cardiac examinations—perspectives along the axes (short axis or long axis) or, respectively, a two-chamber view or a four-chamber view are typically selected, while the indication "L" (for left) or "R" (for right) is selected given an organic, orthopedic examination. It is obvious that the specifications of right/left make no sense in a cardiac examination. In other words: the type of examination and the type of acquired image data has an influence on the ability to select perspectives, and this is taken into account according to the invention. This has the advantage that the user is not confronted with unnecessary or irrelevant perspective selection questions or options. He or she can thus choose only among relevant perspectives or determine a DESIRED perspective. Moreover, errors due to incorrect perspective determinations are thereby avoided.

The "set of selectable perspectives" is a selection of perspectives. This set is image data set-specific and/or examination-specific. In other words, this set is applied to the respective case of the image data to be presented and identifies the selection of relevant perspectives. For example, given a heart catheter examination the perspectives "right"/"left" are not offered, and conversely given a graphical representation of the femur the perspectives "vertical long axis"/"horizontal long axis"/"short axis" are not offered. The same accordingly applies to other anatomical structures, other examinations and/or other medical questions.

In principle, two different application scenarios are provided in the perspective control method according to the invention.

1. Control an initial rendering: in this application mode it is provided that, in principle, the respective perspective for the presentation is selected before the first presentation of the images. In this case, the set of selectable perspectives is determined from the entire set of all perspectives relevant to the application case.

2. Execute a perspective change: in this case, the image data are already presented in a perspective (what is known as the REAL perspective) on the screen, and a perspective change into a different perspective should now be executed. In order to not generate unnecessary displays on the monitor, in a preferred embodiment it is provided that the set of selectable perspectives is determined, wherein the REAL perspective is not taken into account since this is already currently being used, and only a change to different perspectives is reasonable. In this case, in addition to the image status and possible additional data sets the REAL perspective can be taken into account as well for the method step of calculating the set of selectable perspectives. Alternatively, the REAL perspective can also be identified with emphasis as the currently used perspective.

According to the invention, the calculated set of selectable perspectives is no longer displayed in the form of a list structure or in the form of a menu on the screen (as provided in the prior art), but rather is displayed in the form of a symbol. The symbol graphically represents the calculated set of selectable perspectives. The symbol includes a button with a graphical and/or brief written representation of perspectives. A perspective can thereby be represented in the form of a schematic, graphical brief representation, for example in the form of a schematic front view, side view or rear view of a patient. The symbol can also include a text identification, cumulatively with the graphical representation, for example in the manner of "back"/"posterior". The symbol can also be represented as an icon or pictogram. It includes a button to receive control commands. The control commands can be input by the user. Depending on the embodiment, different functions of the button of the symbol can be provided. For example, a button of the symbol can be switchable via a simple mouse click or via a double click. Depending on the configuration, here other functionalities can be selected so that the symbol can also be switched via a keyboard operation. The symbol can likewise be activated by a press and/or swipe gesture on a touchscreen. The symbol thus advantageously includes all selectable perspectives for the respective application case, and therefore all relevant perspectives from the calculated set of selectable perspectives.

According to a preferred alternative embodiment of the invention, in addition to the calculation of the set of perspectives an additional selection process can be added. In the second selection process, a second set of selectable perspectives can be determined from the set of selectable perspectives, which second set further limits the selection possibilities to the respective application case. For example, here the current REAL perspective (which should not be available for selection) can be taken into account. Furthermore, the selection for the second set of selectable perspectives can be based on a syntactic and/or semantic selection of image status data and/or other metadata.

According to one aspect of the invention, a trigger signal can be provided that signals to the computer system that a new image or, respectively, a new image series should be presented. For example, this can be triggered automatically after a loading routine for image data. According to a preferred embodiment, it is provided that the interactive symbol is only shown after detection of the trigger signal at the user interface. This has the advantage that the symbol does not unnecessarily appear on the monitor and divert the user from other tasks. In this case, the symbol appears only in the event that the user must also actually select a perspective in the rendering of image data. For example, the trigger signal can be activated by touching the symbol itself, or after touching a corresponding button for the presentation of image data.

A significant advantage of the achievement according to the invention is apparent in that the generated interactive symbol is intuitively intelligible, and can be operated even without written explanations. For example, complicated translations of the written entries into other languages can therefore be omitted.

The symbol is advantageously shown on the user interface so that it overlays an already-presented image data set in the REAL perspective. The entry of a perspective control signal as an input is necessary in order to render the image data set. In the event that the user does not enter a suitable perspective control signal, the user is requested to do this via a prompt (for example in a pop-up window).

The perspective control signal can be a mouse click or another input signal on the part of the user.

In a preferred embodiment, the perspective control signal is controlled or activated by an action on the part of the user, such as a mouse click or an input at a corresponding input device. Alternatively, this action can be a series of input signals that is defined in the configuration phase. This has the advantage that the user can enter the perspective control signal by a simple action (in particular via a mouse click), and the entry of the perspective control signal then causes the rendering of the image data set to be executed. For specific applications may not require the user to enter the perspective control signal as an input via a provided human/machine interface, but rather the perspective control signal can be automatically derived from other data. For example, if a study that includes multiple series should be displayed, and if the perspective control signal for the series has already been detected, this perspective can be automatically transferred to the other series of the study. A new input entry of the perspective control signal by the user is therefore no longer necessary, and the perspective can be derived automatically from the analyzed data sets.

Alternatively, the perspective control signal can be derived automatically from other data sets. For example, this can be the case when a whole-body acquisition of a "composed"

series should be viewed (thus for example a full body scan in MR or PET examinations that include multiple stations/levels). For example, the user may select the abdomen. According to a preferred embodiment of the invention, the system then offers to the selection possibilities to the user, asking from which perspectives he or she would like to view the abdomen exposures. The user can survey the overview of the fully body scan, and quickly arrive at a defined perspective for a specific body region (abdomen, for example).

However, in a preferred embodiment it can be reasonable to inform the user about the currently used perspective (thus the REAL perspective). In this case, the symbol also includes the representation of the REAL perspective in addition to the set of selectable perspectives that can be used as a basis for the DESIRED perspective. The currently used REAL perspective is preferably shown with an emphasis, for example in bold print or provided with a heavy border or with other marking elements.

In an embodiment of the invention, the symbol is shown at the user interface only for a defined time duration. In the event that no user interaction with the symbol occurs after a pre-set time duration, the symbol can be masked out automatically in order to not unnecessarily divert the attention of the user.

An advantage of the method according to the invention is that it is applicable to both mouse interaction and touchscreen interaction. Furthermore, the method can be very easily transferred to other national languages and internationalized through the graphical or symbolic representation of the perspectives. A further significant advantage is in the context-specific selection of perspectives. This advantage results from the fact that the interactive symbol is individually generated and presented dynamically. In this context, "dynamic" means that the symbol is customized to the respective application case and is thus application-specific or context-specific. Among other things, any or all of the examination type, the respective clinical question, anatomical position information, previous actions, and specific selection rules can be taken into account.

For example, for the presentation of images of a cardiac examination a different symbol is accordingly shown than the symbol given a presentation of images of an orthopedic finding.

The presentation of the perspective selection symbol can also occur "in-place" at a freely selectable or fixed position on the monitor at which the image data are presented, thus "within" the presented image data. It is also possible for the selection to be executed alternatively or cumulatively via a direct manipulation at the displayed image, for example by means of mouse interaction or via a touch gesture (for example a long press).

In a configuration phase, it can be established whether the perspective control signal should be triggered by the symbol and/or via a direct input at the surface (for example via a swipe gesture on the touchscreen).

According to a preferred embodiment, the symbol additionally includes a selectable rendering mode that is taken into account in the rendering and/or display of the image data set in the DESIRED perspective. The "rendering mode" can be an additional selection in the subsequent presentation of the images (in addition to the determination of the perspective). For example, the rendering mode refers to the type of presentation of defined image contents. For example, this can thus be used to set that vessels should be presented sagittally in a VRT or MIP technique (VRT: volume rendering technique; MIP: maximum intensity projection).

What is known as an in-place perspective determination can be controlled via an anatomical context. For example, if a user would like to assess a liver, according to the invention transverse slices of an abdomen (for example) are displayed to the user on the monitor. By a selection among the liver images themselves, the user can control the perspectives and rendering modes that are meaningful for the particular finding task. Notional, generalized and/or thematic representations of the images (herein the abdomen) are typically displayed for this purpose. It is thus possible to directly and immediately manipulate or enter the perspective control signal without a separate menu or the showing of the symbol being necessary.

The rendering of the image data set in the determined DESIRED perspective preferably takes place from a memory, in particular the frame buffer. According to a variant, the method ends after the rendering of the image data set in the defined DESIRED perspective. Alternatively, a specific command for the display of the rendered image data set can be executed at at least one monitor.

In addition to the method described in the preceding, the object of the invention is also achieved by a control unit that, among other things, can be implemented as a graphic processor in a graphic card.

The individual modules or units of the control unit are designated to execute the functions that have been described in the preceding in connection with the description of the method.

The control unit serves to determine perspectives upon rendering of an image data set in a DESIRED perspective at a display device or at a monitor.

The control unit has a detection unit, a memory, a calculation unit, a symbol unit and a rendering unit.

In more complex embodiments of the control unit, additional modules can be provided in order to implement the additional functionalities that have been described in the preceding in connection with the description of the method according to the invention.

Within the scope of the invention, the steps of the method that are mentioned in the preceding need not necessarily be executed in the order described. It is as possible to combine specific method steps or to merge them into one step. For example, the dynamic generation of the symbol and the showing of the generated interactive symbol can be executed in a single method step.

According to the preferred embodiment, nearly all method steps are executed automatically (thus without user interaction). The single user interaction exists in the input of the perspective control signal at the interactive symbol (for instance via mouse click or other input). In other embodiments of the invention, however, this manual input is not required and the perspective control signal is derived automatically from other data sets (in particular the image status). All additional method steps are executed automatically.

Moreover, it is possible to design the method as a client server system so that individual segments of the method described in the preceding can be formed at one instance and the remaining segments of the method can be formed at another instance. The instances can be respective discrete, separate, salable units (in particular computer program products). The method according to the invention can therefore be executed as a distributed system at different computer-based instances (for example client/server instances). With regard to the achievement according to the device, individual units can be formed in the graphic process and other units can be formed in other processor modules.

The present invention also encompasses a non-transitory, computer-readable data storage medium encoded with programming instructions that, when the storage medium is located directly, or in a distributed manner, into a processor or a distributed processor arrangement, cause the processor or the processor arrangement to execute any or all embodiments of the method described above.

BRIEF DESCRIPTION OF THE DRAWINGS

FIG. 1 is a schematic overview of a control unit according to the invention and additional computer-based instances according to a preferred embodiment of the invention.

FIG. 2 is a flowchart of a preferred embodiment of the invention.

FIG. 3 shows an exemplary presentation of a symbol according to an embodiment of the invention.

FIG. 4 shows an exemplary presentation of the symbol using a second exemplary embodiment of the invention.

DESCRIPTION OF THE PREFERRED EMBODIMENTS

The invention relates to the control of a rendering process to present medical image data BD. The medical image data BD can have been acquired by different imaging acquisition apparatuses (for example CT, MRT, ultrasound apparatuses, etc.). Depending on the type of modality and the type of finding, two-dimensional, three-dimensional or multidimensional image data sets BD should be rendered. For this purpose, it is necessary that the user selects a defined perspective or orientation and presentation type depending on the specific context (which, among other things, results from the type of images and the type of finding and/or from the examined organ) so that the image data BD can be presented at a monitor M.

After the start of the system, the image data set BD is initially acquired in Step A. Furthermore, in Step A an image status is detected that is associated with the image data set. The image status registers all parameters that are relevant to the definition of the context. Counted among these are, among other things, the imaging modality, the type of examination (for example heart catheter examination etc.) and the examined organ (the heart, an orthopedic examination of the knee etc.), the type of finding and the anatomical position. Furthermore, additional context data of the image data can be registered. In a preferred embodiment, the image status data are derived from the metadata into the image data. The image data BD advantageously exist in a DICOM format and also include header data in addition to the pure image data. The image status data can then be derived automatically from the header data. This image status—and therefore also a context of the image data—is advantageously taken into account in the selection of the perspective upon rendering the image data BD.

In a second method step B, an access take place to a memory MEM in which are stored rules and possibly additional data. The memory MEM advantageously includes rules that indicate which basic possible and selectable perspectives belong to an image status. These rules are advantageously defined in a configuration phase. This configuration phase is upstream of the execution phase. In the configuration phase it can be determined which parameters are registered and considered as image status. Furthermore, the rules can be defined that associate a set of perspectives with an image status. For example, it can thus be defined that the following perspectives should be selectable given cardiac examinations and the use of a 90°-based cardiac plane designation: short axis, vertical long axis and horizontal long axis. These terms correspond to what is known as a two-chamber view or a four-chamber view in traditional two-dimensional echocardiography. In an examination of the heart, with the perspective control method according to the invention it can be precluded that perspectives that are not relevant or not applicable cannot even be selected, and thus do not even appear on a user interface UI. For example, in a cardiac examination choosing between "right" and "left" makes no sense.

The set of selectable perspectives is calculated in Step C. The rules that are stored in the memory MEM are thereby advantageously accessed. In other words: the calculation of the set of selectable perspectives takes place based on the detected image status that is associated with the respective image data set BD. The set of selectable perspectives is therefore also context-specific.

An interactive symbol S is generated dynamically in Step D. The symbol S serves for the graphical representation of the calculated set of selectable perspectives.

At this point it is to be emphasized that the interactive symbol S is respectively dynamically generated. Depending on which image data set should be rendered and/or displayed, a specifically adapted symbol S appears. The symbol S is a graphical representation of the calculated set of selectable perspectives. Only the relevant perspectives that are reasonable in the respective context of the image data BD are thus displayed as a symbol S for selection. "Dynamic" thus also means that the symbol S has different buttons that represent the selectable perspectives. Different images and/or different applications thus also have different symbols S.

The overlaying of the generated, interactive symbol S on the user interface UI takes place in Step E. The symbol S is interactive, such that the user can determine as a DESIRED perspective a perspective from the set of selectable perspectives by activating specific buttons on the symbol S.

The detection of the perspective control signal thereupon takes place in Step F. The perspective control signal relates to the interaction at the symbol S. Depending on which button the user has selected at the symbol S, a specific perspective control signal is generated that leads to the situation that this signal is relayed to a rendering unit that is determined to render the image data set BD in the determined DESIRED perspective. The rendering takes place in method step G and is based on the detected perspective control signal.

After the rendering in Step G and/or after a display of the image data BD in the DESIRED perspective in Step H, the method can be continued iteratively. In FIG. 2 this is characterized in that the process can also begin anew at Step A as an alternative to ending the method.

In principle, the display of the rendered image data set BD is optional and not absolutely necessary. It is likewise possible that the method ends after the rendering G of the image data set BD. The rendered image data BD are advantageously written to a frame buffer.

The symbol S is generated so that the respective perspective is intelligible solely from the graphical presentation (or the presentation as a pictogram). This has the advantage that the perspective selection is intuitively and easily understandable without an associated text needing to be read and/or translated. Alternatively, the graphical presentation of the buttons of the symbol S can also be further supplemented via written information. The written information can be individual letters (for example "R" for right or "H" for head etc.), which serve as an abbreviated designation.

An example of a presentation of the symbol S is found in FIG. 3. In this embodiment, the symbol S comprises six buttons that are arranged around a central perspective cube. The perspective cube serves to designate the three spatial axes that in this case are designated with "H" (head), "R" (for right) and "F" (for front). The buttons of the symbol S include the perspectives that are relevant to the respective context. In this case, the symbol S includes six buttons that are identified as follows:

R—for right profile
P—for posterior or, respectively, rear view
F—for feet
A—for anterior or, respectively, front view
L—for left profile and
H—for head or, respectively, view of the head.

As is schematically shown in FIG. 3, the individual buttons of the symbol S can be operated per button press on a touchscreen. Alternatively, the buttons of the symbol S can be shown on a conventional monitor M and be operated via mouse clicks or other inputs (keyboard, for example). The size of the individual buttons and the size of the symbol S can thereby be determined altogether in a configuration phase.

As an alternative to the presentation of the symbol S that is shown in FIG. 3, it is likewise possible according to the invention to forego the presentation of the perspective cube so that the symbol S includes only the six buttons that are interactively designed and can be operated or, respectively, activated directly via touching.

An additional alternative is to forego the letter designations on the buttons so that the buttons comprise only the graphical presentation of the perspective or, respectively, orientation or view.

In a further alternative, it is possible to provide the written overlays not only using individual letters but rather to use a complete term here (for example "anterior", "posterior" etc.). Alternatively, the written associations with the graphical symbols can also be shown in the form of a legend in a separate window on the monitor M.

FIG. 4 shows the symbol S in another context. Here the context is a cardiac examination, such that the symbol S comprises other orientations. In this context or, respectively, in this image status, the following set of selectable perspectives is generated:

A—apical
M—MID cavity
B—basal
VLA—vertical long axis or, respectively, two-chamber view
HLA—horizontal long axis or, respectively, four-chamber view For those skilled in the art it is self-evident that the two symbols S shown in FIGS. 3 and 4 are only examples, and that a different medical context leads to a different symbol S with different selectable perspectives.

In the following, a control unit 10 according to the invention is explained in detail with reference to FIG. 1. The control unit 10 can be implemented as a graphic processor in a graphic card 1. The graphic card 1 can comprise additional modules and is associated with a computer 100. The computer 100 interacts with a monitor M at which the image data BD should be displayed.

The control unit 10 comprises a detection unit 20, a memory MEM, a calculation unit 30, a symbol unit 40 and a rendering unit 50.

The detection unit 20 serves as an interface to the computer system, and in particular for detection, loading or provision of the image data set BD. The detection unit 20 is typically only an interface to other medical technology modules and serves to import or provide the image data. The control unit 10 and the method are thus also usable independently of imaging modalities and can be used purely as a visualization method for image data. In an alternative embodiment of the invention, the detection unit 20 can also be an imaging modality. Furthermore, the detection unit 20 serves to detect the image status that is associated one-to-one with the image data set BD. The image status thus identifies a context of the image data and indicates which examination, which modality, which anatomical region the image data BD deals with. The image status or, respectively, the establishment of the parameters that are registered for the image status is determined in a configuration phase.

Rules in order to determine a set of selectable perspectives depending on the detected image status of the detection unit 20 are stored in the memory MEM. In addition to the image status 20, a current REAL perspective of the already rendered image can also be further taken into account in the event that an image has already been presented at the monitor M. In the event that it is an initial image presentation, only the image status is taken into account.

The calculation unit 30 serves to calculate the set of selectable perspectives depending on context. In particular, the image status and/or the REAL perspective are thereby taken into account.

The symbol 40 serves to generate the interactive, advantageously graphical symbol S. The symbol S serves for the graphical representation of the calculated set of selectable perspectives. The symbol S has different interactive buttons, with a respective button being associated with a selectable perspective. The selectable perspectives are context-dependent and application-specific so that they can be generated dynamically and respectively updated for the respective application case of the image data BD. User interactions in the form of perspective control signals can be detected at the individual buttons of the symbol S. For example, it can be detected on which button of the symbol S the user clicks or which button he directly touches on a touchscreen. This is executed by the symbol unit 40. With this the perspective control signal signals which DESIRED perspective should be used in the subsequent rendering of the image data. This perspective control signal is relayed to the rendering unit 50.

In an alternative embodiment of the invention, it can also be provided to increase the recognition effect for the symbol S and to always design it the same so that the user does not need to reacquaint himself. Although the buttons are then selected and/or generated dynamically, the presentation of the buttons is determined according to a coinciding basic scheme. For example, this can be achieved in that the buttons and/or the other elements of the symbol S (for example icons and/or text fields) are selected from a preconfigured set. It is likewise possible to construct the symbol S itself according to a coinciding basic scheme so that the user does not need to reacquaint himself or herself with the format.

The rendering unit 50 serves to render the image data set BD in the determined DESIRED perspective. The DESIRED perspective is thereby based on the detected perspective control signal of the symbol unit 40. At this point it is expressly noted that the DESIRED perspective can also coincide with the REAL perspective, such that in this case no perspective change is implemented in actuality.

In summary, the present invention can be described as a control method that is applied to determine orientations or perspectives in the rendering of the image data set BD in a selected DESIRED perspective. In particular, the context of the image data BD is thereby taken into account via the detected image status. Depending on which image status context is present for the image data BD, different perspectives are offered for the selection at the user interface UI. The selection of the perspectives takes place via the activation of buttons of a dynamically generated interactive symbol S. The buttons of the symbol S graphically represent the selectable perspectives. This can be represented in the form of an exemplary graphical representation of the respective perspective. An overlaying of written perspective designations is possible, but not absolutely necessary. In other words: the respective perspective in which the image data BD should be shown (DESIRED perspective) can be identified and selected exclusively via a graphical representation.

The method can in principle be used in the rendering of image data BD. Alternatively, it can also be applied as a perspective change. In the latter case, the method is designed as what is known as an orientation changer that serves to transform the image presentation in a REAL perspective into the image presentation in a DESIRED perspective. The context or, respectively, the image status of the image data BD is taken into account.

Although modifications and changes may be suggested by those skilled in the art, it is the intention of the inventors to embody within the patent warranted hereon all changes and modifications as reasonably and properly come within the scope of their contribution to the art.

We claim as my invention:

1. A control unit to determine perspectives upon rendering an image data set in a desired perspective for presentation at a display device, comprising:
   a detection unit configured to acquire an image data set in which anatomy of a patient, obtained in an examination of the patient, are represented, and to detect, from the image data set, an image status that designates at least said anatomy and type of said examination;
   a memory in which rules are stored that, when executed, determine a set of selectable perspectives of the anatomy represented in the image data set, dependent on the detected image status and, when present, also dependent on a real perspective of an already-rendered image of said anatomy;
   a calculation unit configured to access said memory and to apply said rules to said image data set to calculate said set of selectable perspectives;
   a user interface comprising a touchscreen;
   a symbol unit configured to dynamically generate, from said image status, a central symbol, and to generate a plurality of interactive symbols that individually graphically represent selectable perspectives in said calculated set of selectable perspectives, and to show said interactive symbols on the touchscreen of the user interface clustered around the central symbol;
   said symbol unit being configured to generate said central symbol as a pictogram dependent on said anatomy and said type of examination designated by said image status, said pictogram representing a plurality of different anatomical directions associated with said anatomy that are relevant for the type of examination represented in the pictogram of the central symbol;
   said symbol unit being configured to show said interactive symbols clustered around said central symbol on said touchscreen at respective locations on said touchscreen that are anatomically correlated with the respective directions indicated by the pictogram of said central symbol;
   said symbol unit being configured to detect at least one perspective control signal generated by a touch at a selected one of the interactive symbols, and to determine the desired perspective therefrom; and
   a rendering unit comprising a rendering processor and a display in communication therewith, said rendering processor being configured to render the image data set in the desire perspective designated by said perspective control signal, and to cause the rendered image data set to be displayed at said display with said desired perspective.

2. A control unit as claimed in claim 1 wherein said detection unit, said calculation unit, said symbol unit and said rendering unit are configured as a graphic processor in a graphic card.

3. A control method to determine perspectives upon rendering an image data set in a desired perspective for presentation at a display device, comprising:
   providing a processor, that is in communication with a user interface having a touchscreen and a display with an image data set in which anatomy of a patient, obtained in an examination of the patient, are represented and, in said processor, detecting, from the image data set, an image status that designates at least said anatomy and a type of said examination;
   storing rules in a memory that, when executed, determine a set of selectable perspectives of the anatomy represented in the image data set, dependent on the detected image status and, when present, also dependent on a real perspective of an already-rendered image of said anatomy;
   from said processor, accessing said memory and applying said rules to said image data set to calculate said set of selectable perspectives;
   in said processor, dynamically generating, from said image status, a central symbol, and generating a plurality of interactive symbols that individually graphically represent selectable perspectives in said calculated set of selectable perspectives, and showing said interactive symbols on the touchscreen of the user interface clustered around the central symbol;
   in said processor, generating said central symbol as a pictogram dependent on said anatomy and said type of examination designated by said image status, said pictogram representing a plurality of different anatomical directions associated with said anatomy that are relevant for the type of examination represented in the pictogram of the central symbol;
   in said processor, showing said interactive symbols clustered around said central symbol on said touchscreen at respective locations on said touchscreen that are anatomically correlated with the respective directions indicated by the pictogram of said central symbol;
   in said processor, detecting at least one perspective control signal generated by a touch at a selected one of the interactive symbols, and determining the desired perspective therefrom; and
   in said processor, rendering the image data set in the desired perspective designated by said perspective control signal, and causing the rendered image data set to be displayed at said display with said desired perspective.

4. A control method according to claim 3, comprising controlling and executing a perspective change in an image that is already presented at a display device, and providing the rendered image data set in a REAL perspective at the display device.

5. A control method according to claim 3, comprising showing the symbols at the user interface overlaid on an already shown image data set in the real perspective.

6. A control method according to claim 3, comprising detecting the image status automatically in said processor from at least one of metadata regarding the image data, data with regard to modality, type of examination, organ, finding, position and context of the image data, and automatically deriving which perspectives are meaningful from the image status data.

7. A control method according to claim 3, comprising generating the interactive, graphical symbols to include a selectable rendering mode that is taken into account in the rendering of the image data set in the desired perspective.

8. A non-transitory, computer-readable data storage medium encoded with programming instructions that, when the storage medium is loaded into a computerized processing system having a user interface comprising a touchscreen, and a display, cause the computerized processing system to:

acquire an image data set in which anatomy of a patient, obtained in an examination of the patient, are represented, and to detect, from the image data set, an image status that designates at least said anatomy and a type of said examination;

access a memory in which rules are stored that, when executed, determine a set of selectable perspectives of the anatomy represented in the image data set, dependent on the detected image status and, when present, also dependent on a real perspective of an already-rendered image of said anatomy;

apply said rules to said image data set to calculate said set of selectable perspectives;

dynamically generate, from said image status, a central symbol, and generate a plurality of interactive symbols that individually graphically represent selectable perspectives in said calculated set of selectable perspectives, and show said interactive symbols on the touchscreen of the user interface clustered around the central symbol;

generate said central symbol as a pictogram dependent on said anatomy and said type of examination designated by said image status, said pictogram representing a plurality of different anatomical directions associated with said anatomy that are relevant for the type of examination represented in the pictogram of the central symbol;

show said interactive symbols clustered around said central symbol on said touchscreen at respective locations on said touchscreen that are anatomically correlated with the respective directions indicated by the pictogram of said central symbol;

detect at least one perspective control signal generated by a touch at a selected one of the interactive symbols, and to determine the desired perspective therefrom; and render the image data set in the desired perspective designated by said perspective control signal, and cause the rendered image data set to be displayed at said display with said desired perspective.

* * * * *